United States Patent [19]

Moser et al.

[11] Patent Number: 4,847,763

[45] Date of Patent: Jul. 11, 1989

[54] LASER AUDIOMETER SYSTEM

[75] Inventors: Ludwig M. Moser, Estenfeld; Anton Kammermeier, Welden, both of Fed. Rep. of Germany

[73] Assignee: Westra Electronic GmbH, Fed. Rep. of Germany

[21] Appl. No.: 18,825

[22] Filed: Feb. 24, 1987

Related U.S. Application Data

[63] Continuation of Ser. No. 627,535, Jul. 3, 1984.

[30] Foreign Application Priority Data

Jul. 19, 1983 [DE] Fed. Rep. of Germany ....... 3325955
Sep. 23, 1983 [DE] Fed. Rep. of Germany ....... 3334524
Feb. 11, 1984 [DE] Fed. Rep. of Germany ....... 3404883

[51] Int. Cl.$^4$ .......................... A61B 5/12; G11B 7/00; G06F 15/42
[52] U.S. Cl. .............................. 364/413.02; 128/746
[58] Field of Search ........................ 128/346; 73/595; 364/415

[56] References Cited

U.S. PATENT DOCUMENTS

| | | | |
|---|---|---|---|
| Re. 31,692 | 10/1984 | Tyburski | 382/65 |
| 3,809,811 | 5/1974 | Delisle | 73/585 |
| 3,820,067 | 6/1974 | Shepard | 340/146.3 |
| 4,224,468 | 12/1980 | Calder, Jr. | 73/585 |
| 4,238,843 | 12/1980 | Carasso | 365/234 |
| 4,284,847 | 8/1981 | Besserman | 73/585 |
| 4,321,427 | 3/1982 | Singh | 128/746 |
| 4,408,291 | 10/1983 | Gunzberg | 364/468 |
| 4,449,198 | 5/1984 | Kroon | 364/900 |
| 4,471,171 | 12/1984 | Köpke | 179/107 |
| 4,476,724 | 10/1984 | Gotze | 73/585 |
| 4,481,412 | 11/1984 | Fields | 235/385 |
| 4,518,361 | 5/1985 | Conway | 364/419 |

FOREIGN PATENT DOCUMENTS

| | | | |
|---|---|---|---|
| 0020745 | 7/1983 | European Pat. Off. | |
| 3113849 | 10/1982 | Fed. Rep. of Germany | 128/746 |
| 2299004 | 1/1975 | France | 128/746 |
| 0030273 | 2/1983 | Japan | 382/65 |

OTHER PUBLICATIONS

"Optical Techniques Light the Way to Mass-Storage Media"; M. P. Blue & D. Chen; Mar. 3, 1969, pp. 108-116.

Primary Examiner—Joseph Ruggiero
Assistant Examiner—Gail O. Hayes
Attorney, Agent, or Firm—Oliff & Berridge

[57] ABSTRACT

An audiometer system for selectively generating audiologic test signals of selectable kind and intensity to be used in audiometric testing of the hearing abilities of persons. A repertoir of test signals and patterns is prestored in a source of test signals, each test signal having a corresponding unique address. Control means including a tablet or a display screen unit enable an operator to manually select desired test signals from said prestored repertoir. The operators selection causes said control means to address said source of test signals so as to reproduce the desired test signals. The source of test signals may be a digital disc player having a removable disc containing said repertoir prestored thereon as digital signal representations.

23 Claims, 6 Drawing Sheets

LASER AUDIOMETER SYSTEM

This application is a continuation of application Ser. No. 627,535, filed July 3, 1984.

FIELD OF THE INVENTION

The present invention relates to signal generation systems, and in particular to interactive audiometric test systems adapted to selectively generate audiologic hearing test signals.

BACKGROUND OF THE INVENTION

Audiometric testing of hearing abilities usually considers two different aspects. The first aspect is to determine the degree of hearing loss throughout the audible frequency spectrum by a test procedure using pure tone frequencies within a given frequency range. For this purpose, a stepped sequence of pure tone frequencies is presented to each of an examinee's ears through earphones, the intensity level at each of said tone freuqencies being varied up and down several times to accurately ascertain the examinee's hearing threshold for each of said tone frequencies.

The second aspect relates to the testing of the ability to discriminate speech signals. For this purpose, selected discrete words of speech are presented to the examinee's ears with varying intensities.

A further aspect is the testing of the examinee's hearing abilities in the presence of background noise. For this purpose, test signals (audio tone signals or speech signals) are individually presented to one of the examinee's ears whilst simultaneously presenting a masking noise to the other ear.

Prior art audimetric systems use two different kinds of apparatus for performing tone frequency testing, on the one hand, and speech discrimination testing, on the other hand.

Such systems for performing tone frequency audiometric testing usually comprise a sine wave generator and means for varying the frequency in predetermined steps and means for varying the output intensity. Prior art apparatus for speech discrimination audiometric testing commonly comprise a magnetic tape deck or a disc player for reproducing test words recorded on a magnetic tape or on a disc. Another known type of audiometric apparatus for reproducing speech signals uses a rotating drum on which the signals are recorded in adjacent tracks.

It is a first object of the invention to provide an audiometric system using only one single apparatus for both reproducing pure tone audio frequency signals for hearing threshold testing and speech signals for speech discrimination testing.

Most of said prior art audiometric apparatus for performing hearing threshold testing using pure tone frequency signals are operated automatically following a given operating program. In such automatic apparatus, a predetermined sequence of stepped tone frequencies is produced, and the apparatus includes a potentiometer which is driven by a reversible motor for intensity variation. At any of said frequencies, the amplitude level is continuously increased until the examinee hears the signal. As long as the examinee can hear the signal, he pushes a button causing the amplitude level to decrease again until the signal fades from audibility. Upon release of the button, the signal fades into audibility again. This cycle is repeated several times at any given frequency to ascertain the examinee's hearing threshold. Simultaneously, the entire test sequence is recorded by a synchronously coupled automatic recorder.

However, while such automatic audiometer apparatus has proved satisfactory for routine testings, for example in industrial medicine where employees who must work in noisy environments have to undergo frequent and regularly scheduled hearing tests to prevent ear damage, such automatic audiometer apparatus has not proved efficient in performing thorough audiologic testing as a basis for accurate individual matching of a hearing aid.

Efficient audiologic testing requires operating facilities enabling the examiner to individually select or repeat appropriate test signals, on the one hand, and requires most simple operation of the apparatus, on the other hand, to enable the examiner to pay his full attention to the examinee to observe his reactions and also to take into account such circumstances as the examinee's age, intelligence, concentration and tiredness.

A second concern is to provide an audiometer system which is most simple to operate and allows for individually selected sequences of test signals.

While some tone audiometers are known having manually operable control means for varying the frequency and the amplitude level of the test signals by the operator, free selection of any available test word is very difficult in prior art speech audiometers of the above-mentioned types using a magnetic tape or a disc as a storage medium. It is very difficult to find a special test word recorded anywhere on a magnetic tape within a reasonable time even when a band counter is used, and even the simple repetition of a special test word involves the problem that the tape cannot be rewound exactly enough to prevent that the word will be repeated only in part or together with the end of the preceeding word. The same applies when using a disc player. While it is easier to find a special test word in a speech audiometer using a rotating drum on which the individual test words are recorded in separate adjacent tracks, such type of audiometer suffers from the disadvantage that it is very bulky.

Thus a further concern is to provide an audiometer system which includes audiometric speech discrimination testing, allowing for quick and exact selection of any one of a number of available test words recorded on a storage medium.

Further problems of prior art audiometers referred to above include problems of noise, wear of the magnetic tape or of the phonograph record, signal distortion and non-linearity. Especially in speech discrimination testing, background noise is a major problem causing a high noise to signal ratio specifically at the low intensity levels required for such testing.

Moreover, measurements have shown that many existing audiometers suffer from imperfect operation due to harmonic and other distortions.

Therefore, the audiometer system must generate high quality audiologic test signals with minimum background noise and minimum signal distortion.

SUMMARY OF THE INVENTION

According to the present invention, an audiometer system is adapted to selectively generate audiologic test signals with a laser-optical read-out digital storage disc player for reading out test signals digitally recorded on a disc, wherein said disc player is either a compact disc audio player or a video disc player. Furthermore, the system comprises a digital processor connected to one disc player and adapted to control said disc player to read-out selected test signals in response to an operator's manual commands or, if desired, in accordance with a predetermined program. The digital processor has associated therewith a memory adapted to store table of contents information of available test signals recorded on the disc, the information being also recorded on the disc and being read-out from the disc before starting the audiologic testing procedure. An operator's command unit is connected to said processor and adapted to provide request signals indicating the selected test signal.

The audiometer system according to the present invention offers a number of great advantages. First of all, all kinds of testing irrespective of whether pure tone testing or speech discrimination testing can be performed with one single audiometer system, and all known types of tests can be performed with this new audiometer system including any kind of future test developments. Furthermore, any kind of distortions of the test signals is excluded. Moreover, any kind of phase-relationship between two or more related test signals in a multiple channel recording is possible with absolutely perfect accuracy. The testing procedure can be easily conducted enabling the examiner to put his full attention to the examinee due to the easy operation of the new audiometer system allowing for quick and exact selection of any one of a nmber of available test signals recorded on the disc.

Use of a video disc player offers particular advantage in case of audiologic testing of the hearing abilities of children. In this case, the video disc player can be used both to reproduce audible audiologic test signals and visual pictures to stimulate the children's active cooperation in the audiologic procedure.

Preferably, the audiometer system is a dual channel system comprising a dual channel disc player, one channel being adapted to selectively generate audiologic test signals to one of a pair of earphones, and the other channel being adapted to selectively generate audiologic mask signals to the other earphone.

In one embodiment, said operator's command unit comprises a tablet on which a schedule of identifications of the available test signals is provided. The tablet has associated therewith a command probe which is movable on the tablet by the operator to select any one of the identifications scheduled on the tablet. The identifications may be provided both in a visually and computer readable form so that the command probe may be adapted to read the identifications to provide a respective address signal to the digital processor.

In a modification, the command probe may be adapted to activate the tablet by touching the tablet at the area of the selected one of the identifications, and the tablet may comprise identification grid means adapted to be operated by the probe using either mechanical pressure or magnetic, inductive or capacitive coupling when touching the tablet so as to cause said tablet to provide a respective address signal to the digital processor.

The schedule of available test signals may be printed on a form sheet made of paper or plastics foil material, and the tablet may have a frame for holding such printed form sheet. If desired, several different kinds of printed forms may be used alternatively to perform different test procedures. Appropriate program control of said digital processor ensures correct interpretation of the address signals received from the tablet in accordance with the respective type of printed form used in the tablet. Preferably, the printed form is also used for recording test results.

Operation of the audiometer system by means of said printed form sheets will avoid misoperation of the system.

The tablet or the printed form sheet or a transparent cover sheet attached to the tablet and covering said printed form sheet may be provided with suitable means such as grooves for guiding said command probe when it is moved manually.

Operation of the new audiometer system using said printed forms will avoid misoperation of the system. Furthermore, the single all-round audiometer system provided by the present invention can be made any kind of specialized audiometer simply by use of a corresponding printed form sheet. The control of the audiometer system by means of said form sheets allows for easy and quick access to every compact disc stored test.

Preferably at least two different kinds of printed form sheets are provided to allow for different kinds of testing procedures, for example hearing threshold testing or speech discrimination testing. The frame for holding the printed form sheet may then include form recognition means adapted to recognize the presence and the kind of a form sheet on the tablet. The form sheet may be provided with a binary code index such as printed binary code labels thereon and said form recognition means may comprise optical sensing means, preferably miniature reflection photoelectric devices including a light-emitting diode and an adjacent light-sensitive semiconductor element responsive to reflected light. The incorporation of an interval timer circuit operating said optical sensing means only during successive short periods with intervals therebetween will greatly prolong the lifetime of the sensing means.

In a second embodiment, the operator's command unit comprises a display screen unit adapted to display on its screen a schedule of visual identifications of available test signals, and the unit has associated therewith identification means adapted to selectively identify any of the identifications displayed on the screen so as to provide a respective address signal to the digital processor. The identification means may comprise a cursor movable on the screen and a control device for controlling movement of the cursor, which control device may be a keyboard, a control lever adapted to be moved in a cross-like pattern to cause up and down or left and right movement of the cursor, or it may comprise a sensor unit and in combination therewith an identification raster plate on which the sensor unit is freely movable, the sensor unit generating in response to its movement on the plate a control signal causing the cursor to be moved in correspondence to the sensor unit movement.

In an alternative embodiment, the identification means may comprise a probe causing the generation of the address signal by touching the screen at the region displaying the selected identification.

Compact disc digital audio players and digital video disc players are commercially available and have been developed for improved hifi or video quality in the audio and video entertainment field.

The compact disc digital audio technique employs a non-contact signal read-out system using a semiconductor laser. The digital code recorded on the disc does not only contain signal information but contains also clock bits for speed control and address information allowing to search any desired location on the disc. Written in the lead-in area is a table of contents information which is a time information including the start time of each selection as well as the total number and playing time of selections recorded on the disc. The same applies to the digital video disc technique which is similar to the digital audio disc technique. The technique of recording the digital signal and clock information and the use of the table of contents information is known per se and does not constitute a part of the invention. Further technical details are incorporated by reference from the Compact Disc Repair Manual CDP-101, Part No. 9-951-028-11 of Sony Corporation, Technical Suppot Department.

It is the basic idea of the present invention to incorporate such laser-optical read-out disc player into an audiometer system. In this way, the advantages of such laser optically read-out digital disc technique can be utilizied in audiometric testing. The advantages of the digital disc technique include an extremely wide dynamic range of 90 decibel throughout the entire audible frequency spectrum, an extremely linear frequency response, an extremely low harmonic distortion which is never worse than 0.01%, and wow and flutter being too minute to be measured. These characteristics of the digital disc technique are by far superior to prior art LP-disc players or tape recorders. Especially, the dynamic range and the harmonic distortion of the digital disc system are at least by a factor 100 better than the best values of prior art disc players or tape recorders. Moreover, any location of the digital disc is immediately accessible due to the time code function incorporated into the digital data recorded on the disc. Since a laser-optical pick up is used, no wear occurs neither at the disc nor at the pick up system so that the quality of reproduction will not suffer even after frequent use of a disc.

The incorporation of such laser-optical read-out digital disc technique results in a great improvement of the audiologic testing procedure. Very accurate test signals can be reproduced without any background noise and without any loss of quality after extended use of the system. In an audiologic speech discrimination test, any desired test word recorded at any location on the digital disc is accessible within an extremely short period.

Using commercially available components such as the digital disc player and digital processor, memory and command unit components available from the computer industry, allow for very economic production of the laser audiometer system according to the present invention requiring only minor adaptions and modifications of said components.

In addition to the above-mentioned features, the audiometer system according to the present invention may comprise a device for protecting the examinee against excessive intensity of test signals which may erroneously be requested by the examiner, for example, by misoperation of the command unit. The protecting device may have an electro-acoustic transducer, for example a microphone, monitoring the examinee and means for attenuating intensity of the signal in response to an output signal of the transducer when an audible reaction of the examinee, for example a cry of the examinee, is received.

As explained above, the main object of the invention was to provide an improved audiometer system capable of reproducing easy accessible and best quality test signals for audiologic test procedures to be achieved according to the teaching of the present invention by incorporating a laser-optical read-out digital disc system.

In accordance with a further aspect of the present invention, such a signal reproducing system can be used not only as an audiometer system but, due to its superior characteristics as mentioned above, may be used also in the measuring or control field as a signal source for generating high accuracy measuring or control signals of any desired wave form. The required signals may be, as it is the case in the audiometer system, recalled manually at will from the available stock of signal wave forms recorded on the disc, or alternatively the required signals may be recalled under control of a predetermined program.

The signals to be generated by such measuring or control signal generating system may be audio frequency signals, for example for testing and adjusting the transfer characteristics of hearing aids or for taking acoustic measurement in buildings, or the signals may be frequency or intensity reference signals, for example for calibration or comparison purposes, frequency response measurements or distortion factor measurement.

Moreover, the invention can be used even in the medical field, for example for high accuracy generation of electrical signals for heart and lung stimulation.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
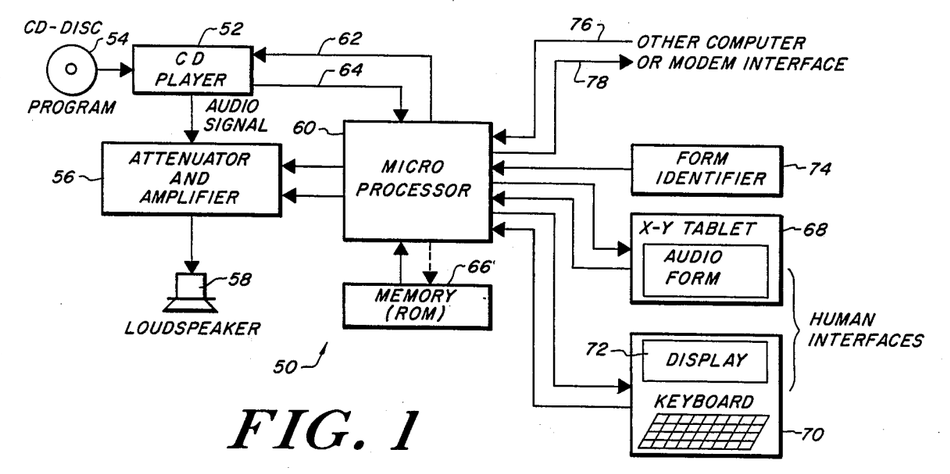
FIG. 1 is a block diagram of an audiometer system according to the invention.

FIG. 1 shows a block diagram of an audiometer system 50 according to the invention. The system 50 includes a compact disc player 52 for selectively reproducing audiologic test signals stored in digital form on a compact disc 54. The output audio signal of the compact disc player 52 is applied to an attenuator and amplifier unit 56 in which the audio signal is attenuated or amplified to the selected intensity level. The output signal of the attenuator and amplifier unit 56 is then applied to a loudspeaker 58 for conversion to an audible sound signal.

The operation of the compact disc player 52 and of the attenuator and amplifier unit 56 is controlled by a microprocessor 60 by signals on leads 62 and 64 said microprocessor 60 having associated therewith a memory 66. The compact disc 54 has also recorded thereon table of contents and program information which may be used internally, discussed below, or read out by the compact disc player 52 and transmitted to the microprocessor 60.

The memory 66 may generally be a random access memory (RAM) which allows to store in a table of contents and system 50 program information read out from the compact disc. However, for economical reasons, it is preferred to use a read only memory (ROM) which is programmed in accordance with the compact disc to be used. Conveniently, such read only memory is removably mounted on a printed circuit board by means of a plug-in socket arrangement so as to allow easy replacement of the memory module in the event a different kind of compact disc or disc format shall be used, requiring a corresponding different memory.

Operator's test instructions may be applied to the microprocessor 60 through one of two human interface units connected to the microprocessor. One of such human interfaces is an X-Y tablet 68 which is adapted to hold a printed form sheet having printed thereon a schedule of available test signals, and said tablet may comprise an identification grid means which may be activated by touching said form sheet on the tablet at the location of the selected signal identification by means of a stylus so as to cause said tablet to provide a respective address signal to the microprocessor. The identification grid means within said tablet may be activated by mechanical pressure applied by said stylus or by inductive or capacitive interaction between said stylus and the tablet.

The other human interface is a keyboard 70 with display unit 72 which allows to address the microprocessor through the keyboard. The display unit 72 screen may be used to display a schedule of available test words or other test signals or to display the results of the audiologic test procedure.

Of course, the system may be operated with only one of said two human interfaces 68, and 70, 72 while the incorporation of both or additional interface units to be used alternatively is optional. It is, of course, also possible to use any other kind of an appropriate operator's command unit instead of or in addition to the interfaces 68 and 70, 72 shown in FIG. 1 for providing the operator's test instructions to the microprocessor, such as the command units shown in FIGS. 5 and 6 to be described hereinafter.

The X-Y tablet 68 may have associated therewith a form identifier 74 which is adapted to recognize whether a form sheet is present at all on the tablet 68 and, if several different forms are available, what kind of form is present. This form identifier may comprise optical or other sensor elements and is also connected to the microprocessor 60 to povide a respective form identification signal to the microprocessor.

If desired, other computer or modem interface components, for instance for remote data transmission, may be connected to the microprocessor through leads 76 and 78.

Figure 2:
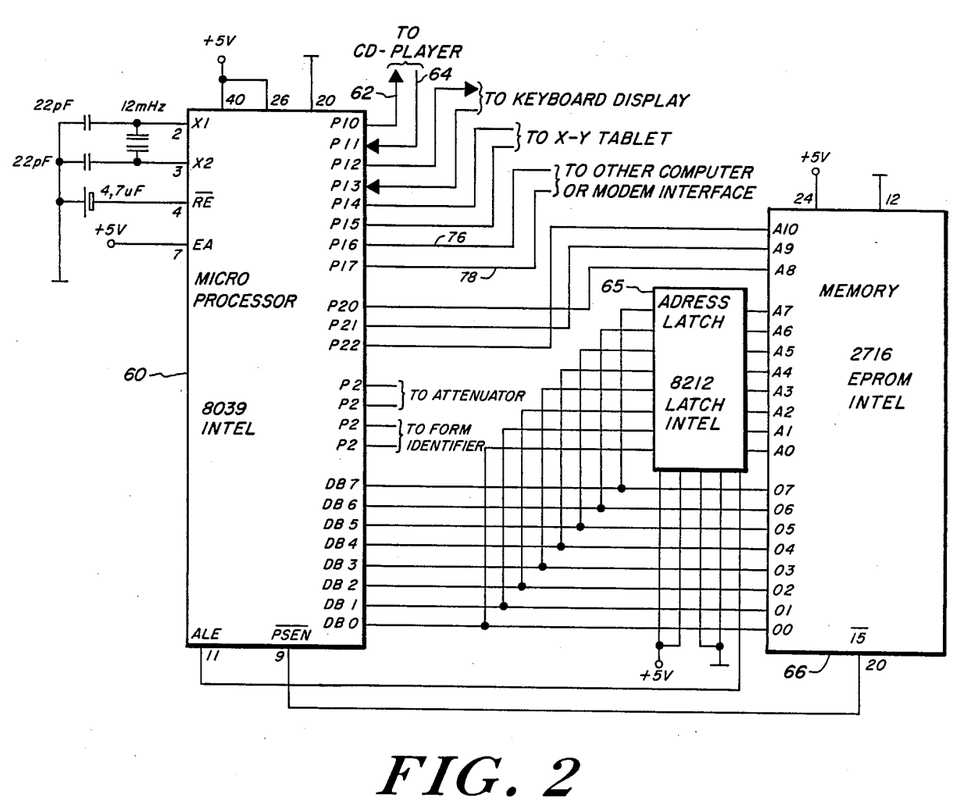
FIG. 2 is a more detailed circuit diagram of the microprocessor and memory components of the system shown in FIG. 1.

FIG. 2 is a more detailed circuit diagram of the microprocessor 60 and memory 66 components of the system shown in FIG. 1.

The microprocessor 60 may be a 8039-Intel microprocessor module and is operable according to the description provided by product description by Intel Corporation, Santa Clara, California, in the MCS-48 User's Manual, dated 1979, herein incorporated by reference. The memory is a ROM 66, for instance a 2716-EPROM-Intel module and has associated therewith an address latch module 65 which may be a 8212-Latch-Intel module.

The wiring connections between these modules and to the other components of the system and the external discrete circuitry associated with said modules is as indicated in FIG. 2.

For reading out data from the read only memory, the microprocessor addresses the memory by applying an address latch enable signal through its output ALE to the address latch module and by simultaneously transmitting the address code through data buses DB0 to DB7. The address latch module receives and stores the address code and applies the address code to the memory through address inputs A0 to A7. Thereafter, the microprocessor enables the memory by transmitting a program store enable signal through its output PSEN to the memory, and the required data are then transmitted from data outputs O0 to O7 of the memory module to data buses DB0 to DB7 of the microprocessor.

Figure 3:
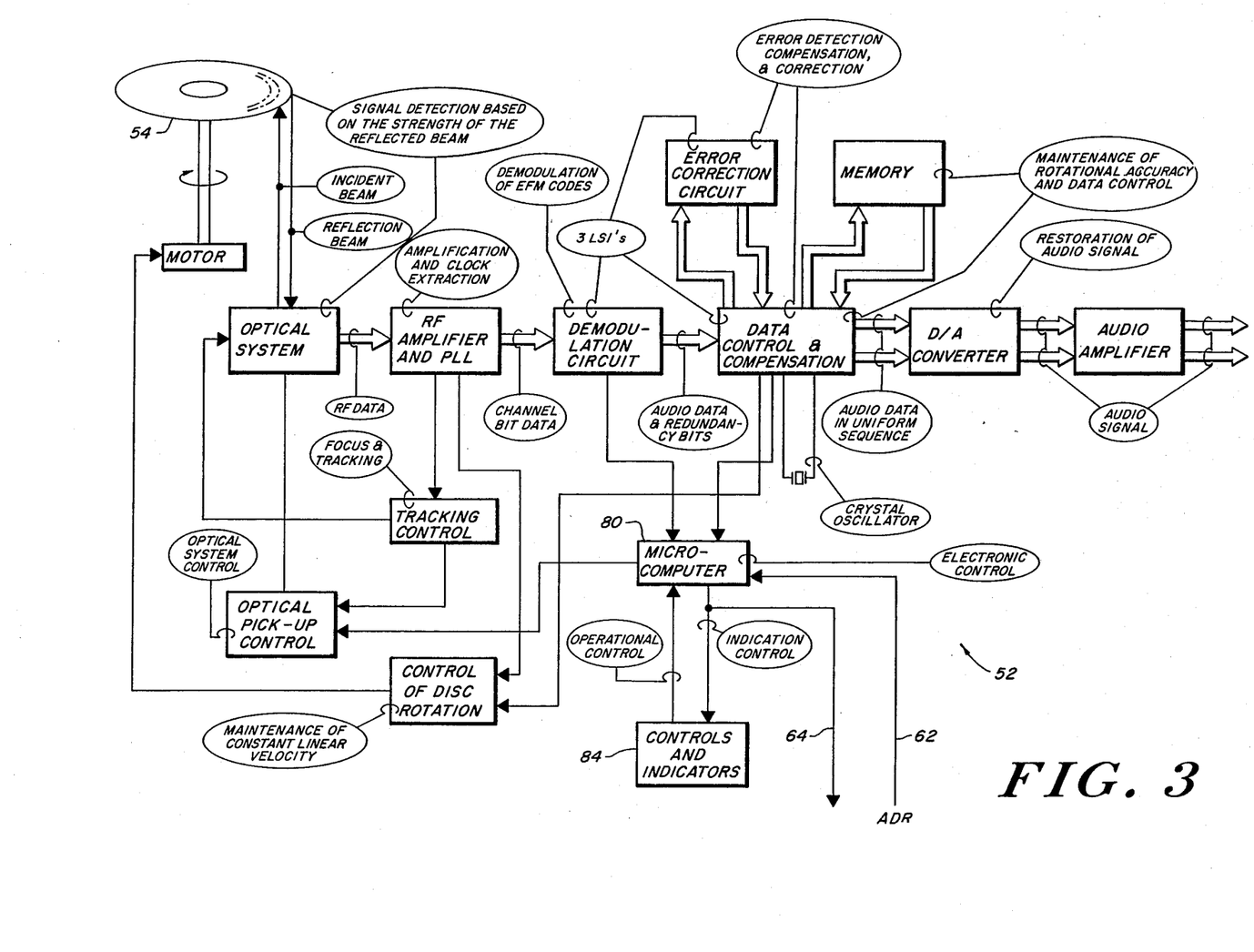
FIG. 3 is a block diagram of a typical compact disc player showing points of connection to the circuitry of FIG. 2.

The microprocessor 60 communicates with the disc player 52 of FIG. 3 by leads 62 and 64. The disc player 52, shown in FIG. 3 is manufactured by Sony Corporation, wherein the instruction and maintenance manuals are incorporated by reference herein. Briefly, the microcomputer 80 receives data location (address) and disc control information from the disc 54 itself and is operative in response thereto, and further in response to controls 84 and signals from microprocessor 60 on lead 62. Similarly, the disc player microprocessor 80 provides control indication back to the system microprocessor 60 on lead 64 according to the format specified by the disc player 52.

Figure 4:
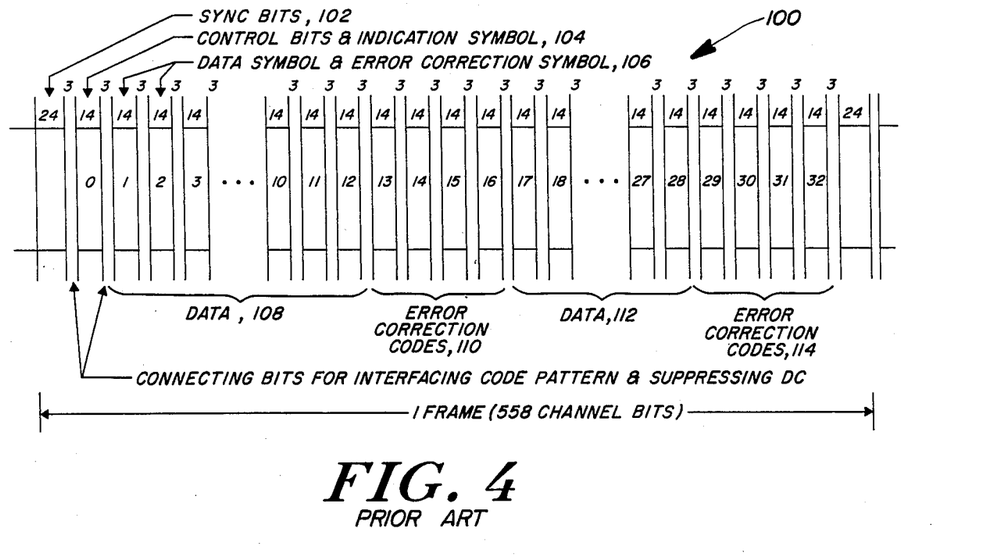
FIG. 4 is a diagram showing the data format of a frame of digital signal recording of the compact disc.

The disc player 52 receives and decodes data stored on the disc 54 having a sequence of data frames 100, as shown in FIG. 4. Each frame 100 comprises a sequence of sync bits 102, control bits 104, data symbol and error correction symbol bits 106, first data bits 108, first data error correction code bits 110, second data bits 112 and second data error correction code bits 114. Presently, the frame 100 includes a total of 558 channel bits which include other reserved or unused bit assignments. However, the system is not in any way restricted to a particular format of data storage.

The information stored on the disc 54 is listed in a stored table of contents which is initially transferred to disc microprocessor 80 after the respective disc 54 is loaded into the disc player 52. The table of contents, specified by the disc player manuals, can specify 1-99 programs. Each program may be further divided into 10 subprograms and appropriately indexed. Moreover, each frame is individually identified by a frame time code contained within the sync bits 102. The program, subprograms and frame time codes are decoded by the disc player microprocessor 80 (or system microprocessor 60) and are accessed by instructions received by signals on leads 62, and otherwise as discussed above.

Figure 5:
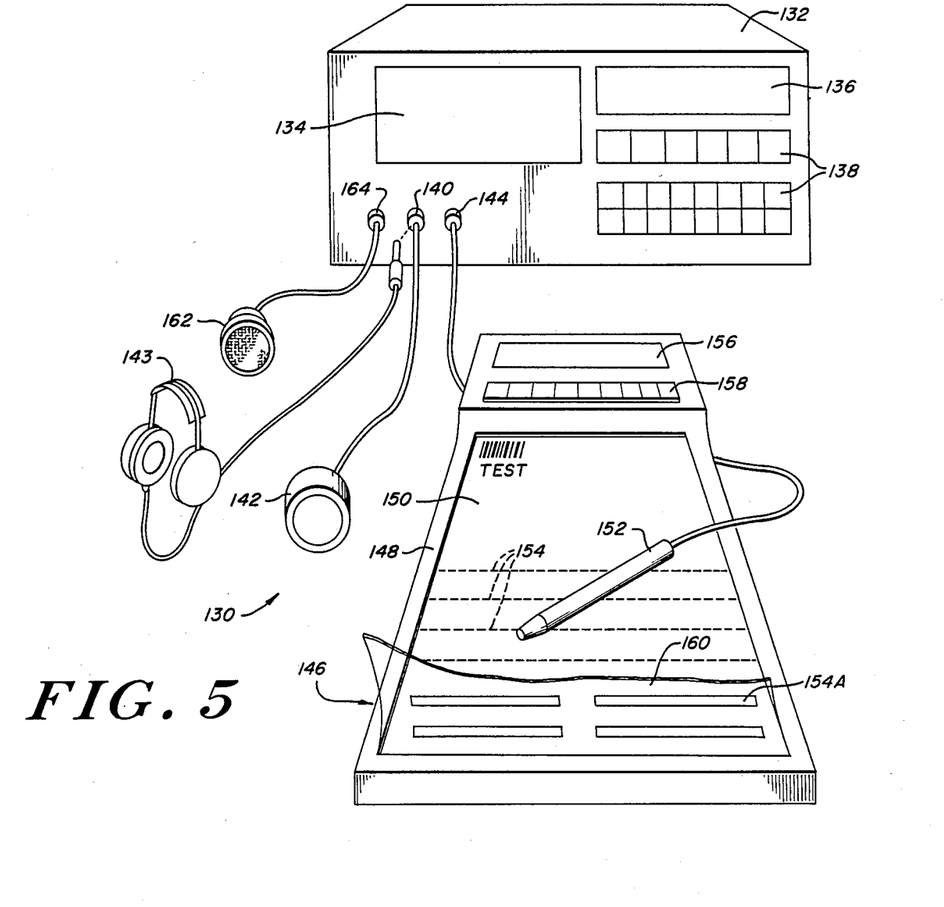
FIG. 5 is a perspective view of an audiometer system according to the invention having an identification tablet as an operator's command unit.

Referring now to FIG. 5, there is shown a perspective view of an audiometer system 130 according to the invention. A housing 132 contains the compact disc player 52, the attenuator and amplifier unit 56, the microprocessor 60 and the memory 66 shown in the block diagram according to FIG. 1. The housing 132 has at its front panel a terminal socket 140 for connecting a loudspeaker 142 and a terminal socket 144 for connecting an operator's command unit 146.

Said command unit 146 comprises a tablet 148 adapted to receive a printed form sheet 150 on which a schedule of available test words or other test signals is provided both in a visually and computer readable form. One example of such a test word is the word "test" indicated on the left top end corner of the form sheet both in visually readable letters and in a computer readable form, for instance as a bar code. The computer readable code is an address code associated to the respective visually readable word which code, when read by means of a bar code stylus 152 or any other suitable reading probe or stylus connected to the tablet 146, causes the tablet to provide a respective address signal through terminal socket 144 to the microprocessor incorporated in the housing 132 to request reading out of the respective test word from the compact disc 54 by the compact disc player 52 also incorporated in the housing 132.

The top portion of the tablet 146 may be provided with a display 156 for monitoring the function of the tablet and, if desired, with an operating keyboard 158, for instance for mode selection if several different modes of operation are provided.

The tablet 146 may also be provided with a transparent cover foil 160 for covering the form sheet 150, and said cover foil 160 may have windows or punched grooves 154A for guiding the bar code reading stylus 152. Alternatively, the form sheet 150 itself may have formed grooves 154 for guiding the stylus 152, in which case the computer readable address code is printed within or relative to such grooves.

The housing 132 has mounted at its front panel a cover which may be opened to insert or to remove the compact disc 52, and a display field 136 and operating keys 138 are also provided at the front panel. Furthermore, a microphone 162 is connected to a terminal socket 164 at the front panel of the housing 132 which microphone is a part of an automatic intensity level reduction device which is operable in case that an unacceptable high intensity level is caused to be reproduced by the system due to accidental misoperation of the system by the operator. The microphone 162 receives any audible reaction of the examinee when the signal level applied to the examinee's ears exceeds the pain threshold so as to reduce the intensity level immediately without needing any action of the operator.

Similarly, a binaural headphone 143 may replace loudspeaker 142 (or 58 of FIG. 1) to provide operator control of the test with respect to each ear channel by keyboard 158, 138, or 58, or by program material stored on disc 52. For example, a test signal may be applied to the left ear channel, while a masking noise or tone is applied to the right ear channel.

Figure 6:
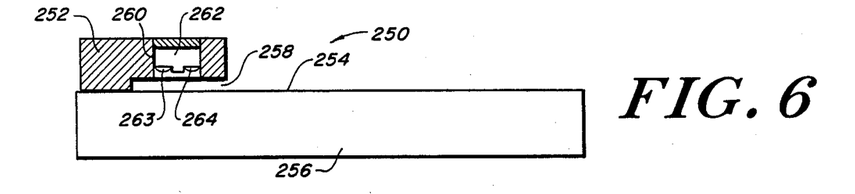
FIG. 6 is a cross-sectional view of a form identifier.

As already mentioned above with reference to FIG. 1, the system may also include a form identifier for recognizing whether a form sheet is present at all on the tablet and what kind of form is present. FIG. 6 shows a cross-sectional view of one embodiment of such a form identifier which may be incorporated into the tablet 146 shown in FIG. 5 or which may be used in similar manner in any other embodiment of tablet, for instance with a tablet integrated into an operator's desk.

The form identifier 250 may comprise a ledge 252 extending along one edge of the upper surface 254 of the tablet 256. The ledge 250 is provided with a recess 258 so as to form a corresponding gap between said ledge and the upper surface of the tablet 256 to receive the corresponding edge of a form sheet not shown. The ledge 252 has a row of four or five holes 260, each of which having mounted therein miniature reflection photoelectric device including a light-emitting diode 263 and an adjacent light-sensitive semiconductor element 264 responsive to reflected light. The edge of the form sheet has printed thereon binary code identifications in the form of a black spot or a void at locations corresponding to those of said photoelectric devices 262. Thus, if in use a void (white paper) is located beneath the photoelectric device 262, light emitted by diode 263 will be reflected and received by the light-sensitive semiconductor element 264. However, if a black spot is present underneath the photoelectric device 262, no light will be reflected by the black spot and received by the light-sensitive semiconductor element. In this manner, the row of photoelectric devices 262 can be used to scan a binary code information, the number of digits corresponding to that of the photoelectric devices 262. This form identifier is able to detect not only the kind of a form sheet lying on the tablet 256 but can also be used to detect whether at all a form sheet is present on the tablet. Dependent on whether the upper surface 254 of tablet 256 underneath the photoelectric devices 262 is made light reflecting or nonreflecting, the detection of reflected light at all photoelectric devices 262 or nondetection of any reflected light at any of said photoelectric devices will indicate that no form sheet is present on the tablet provided that such code combination is not used as a printed form identification code on any of the available form sheets. Said miniature reflection photoelectric devices may be of the type SFH900 manufactured by Siemens Aktiengesellschaft.

Figure 7:
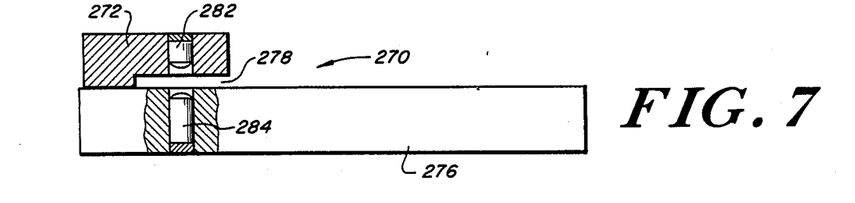
FIG. 7 is a cross-sectional view of a modified form identifier.

Alternatively, the form sheet may have punched binary code identifications at one edge thereof. In this case, a modfied form identifier 270 is used as shown in FIG. 7. This modified form identifier 270 has again a ledge 272 with a recess 278 extending along one edge of the tablet 276 similar to the embodiment shown in FIG. 6. The ledge 272 has mounted therein a number of light emitting diode 282 adapted to direct a beam of light onto the index locations of the form sheet edge to be positioned within the gap formed by recess 278. Opposite to said light-emitting diodes 282, the tablet 276 has mounted therein a corresponding number of light-sensitive semiconductor elements 284 responsive to light transmitted through index punchings of the form sheet.

The operation is similar to that of the form identifier shown in FIG. 6.

Although the photoelectric devices of the form identifiers according to FIGS. 6 and 7 may be operated continuously, it is preferred to operate them discontinuously in predetermined intervals, for example every two seconds for a period of some milliseconds, to achieve a prolongated life time. This may be accomplished using an interval timer circuit of any type well known in the art.

As a further modification not shown, the binary code index of the form sheet may comprise magnetic identifications or conductive areas and the sensing means may comprise magnetic reading elements or capacitive or mechanical contact sensors.

Figure 8:
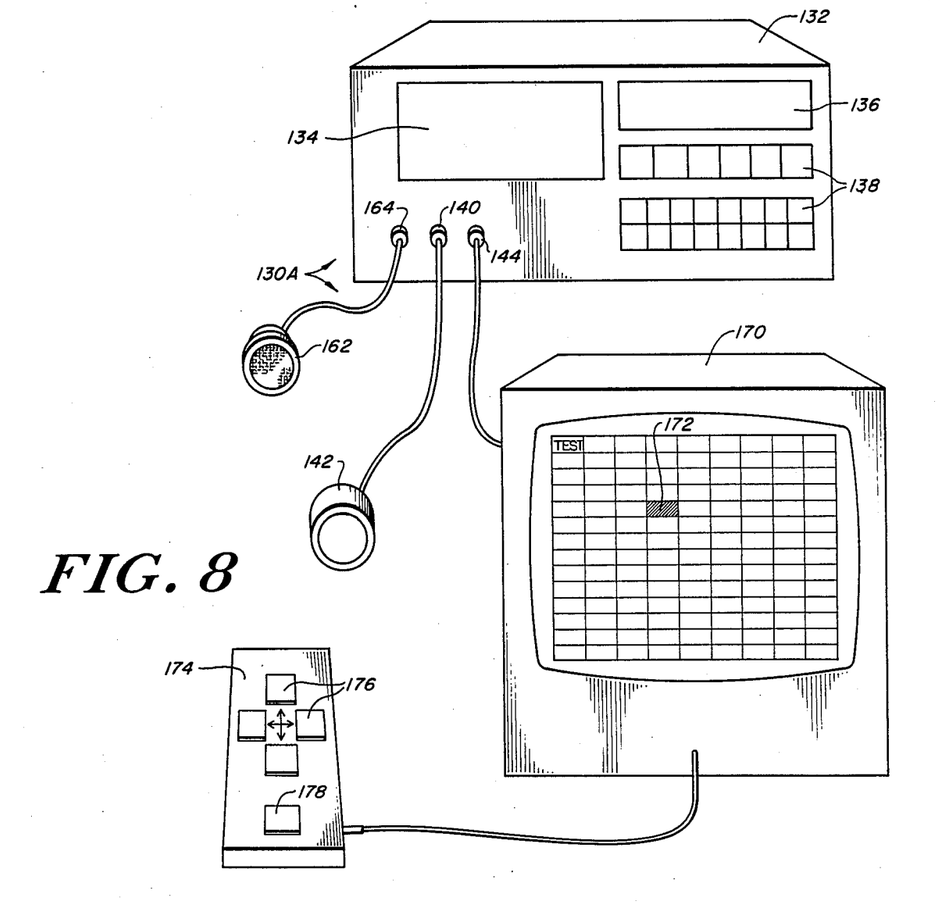
FIG. 8 is a perspective view of an audiometer system according to the invention having a display screen unit as an operator's command unit.

FIG. 8 shows a perspective view of an arrangement 130A similar to that of FIG. 5, except that a display screen unit is used as an operator's command unit instead of the tablet shown in FIG. 5. The housing 132 containing the compact disc player 52, the attenuator and amplifier unit, the microprocessor and the memory, the front panel of the housing with the cover 134, the display 136, the operating keys 138 and the terminal sockets 140, 144, and 164, the loudspeaker 142, and the microphone 162 are the same as in FIG. 5.

The display screen unit 170 is adapted to display on its screen a schedule of available test words or other test signals as indicated by the word "test" in the left top end corner of the screen. Any one of the signals indicated on said schedule may be identified by a cursor 172, and the display screen unit 170 has associated therewith a manually operable control device 174 with a set of four keys 176 for selection of up and down or left and right movement of the cursor 172 on the display screen. After the cursor 172 has been moved to the selected test signal identification on the screen, a further key 178 of the control device 174 can be pressed to cause the display screen unit 170 to provide a respective address signal through terminal socket 144 to the microprocessor for reading out the respective test word or test signal from the compact disc (54).

Of course, any other kind of control device 174 may be used for moving the cursor 172 on the screen.

Figure 9:
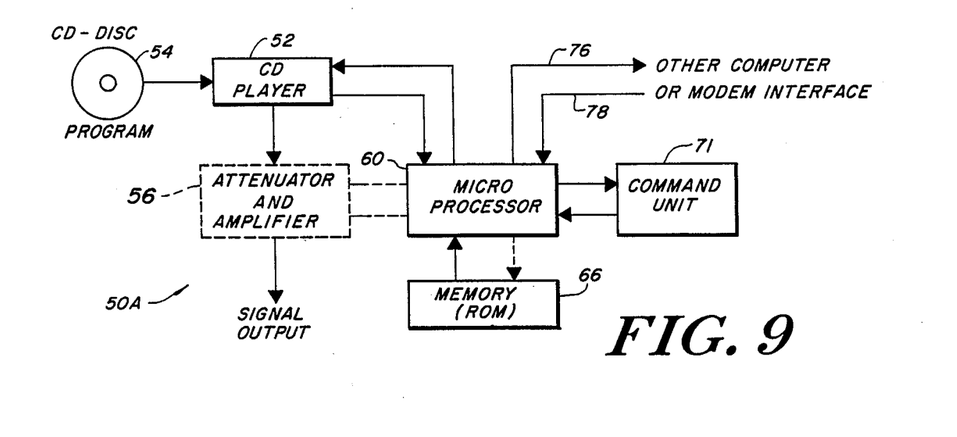
FIG. 9 is a block diagram, similar to FIG. 1, of a signal generation system according to the invention for generating high quality signals for measuring or control purposes.

Referring now to FIG. 9, there is shown a block diagram 50A of a signal generation system according to the invention adapted to generate high quality signals of any wave form for measuring or control purposes. Similar to the system 50 shown in FIG. 1, the system according to FIG. 9 comprises a compact disc player 52 for reproducing signals recorded in a digital form on a compact disc 54, a microprocessor 60 adapted to control the operation of the compact disc player 52, and a memory 66 for storing table of contents and program information necessary to gain access to the desired signal wave forms recorded on the disc 54. If an intensity level control of the output signal reproduced by the compact disc player 52 is desired, an attenuator and amplifier unit 56 can also be used similar to the system in FIG. 1, as indicated in dotted lines.

The memory 66 is conveniently again a read only memory (ROM) which is programmed in accordance with the compact disc 54 to be used. However, if desired, a programmable memory can be used which allows to store in table of contents and program information read out from the compact disc.

Instead of human interfaces which are specifically adapted to an audiologic test procedure, as shown in FIG. 1, the system shown in FIG. 9 has any kind of appropriate command unit 71 connected to the microprocessor 60 for transmitting an operator's instructions to the microprocessor. Alternatively, the system can be operated automatically under control of an operating program which may also be recorded on the compact disc 54 and may be stored into the memory if a programmable memory is used.

FIGS. 10 to 15 show several different kinds of uses of a system according to FIG. 9.

Figure 10:
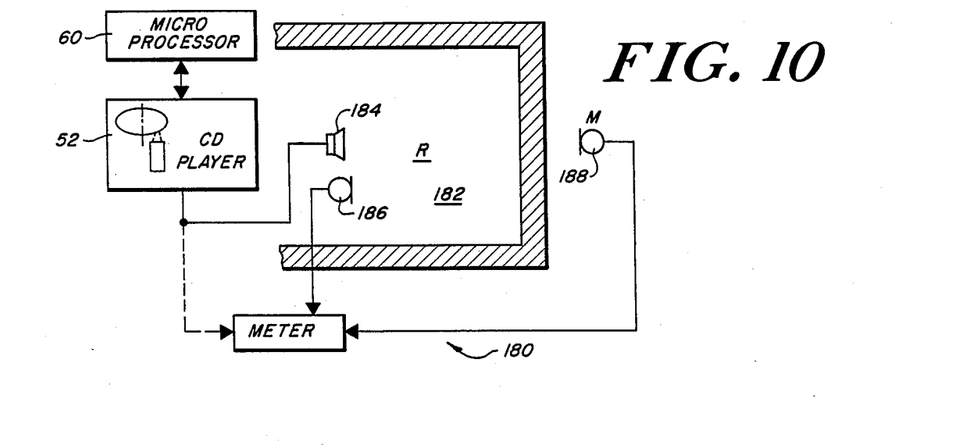
FIG. 10 is a schematic diagram of the system shown in FIG. 9 in use for taking acoustic measurements in a building.

In FIG. 10, there is shown an arrangement 180 for taking acoustic measurements of a room 182 in buildings. A signal generation system according to FIG. 9 is represented only schematically by its main components, namely compact disc player 52 and microprocessor 60 while other components are omitted for clarity. The output signal reproduced by the compact disc player 54 is applied to a loudspeaker 184 arranged in a room 182 the acoustic characteristics of which are to be measured. Microphones 186, 188 may be positioned at one or more appropriate locations inside or outside said room 182 to receive reflected or transmitted sound. In this manner, sound absorption or sound transmission properties of the walls of the room 182 can be measured. The microphones are connected to a meter for measuring the intensity or other parameters of the received sound. If desired, the output signal of the compact disc player 52 may also be applied directly to the meter, as indicated by a dotted line.

Figure 11:
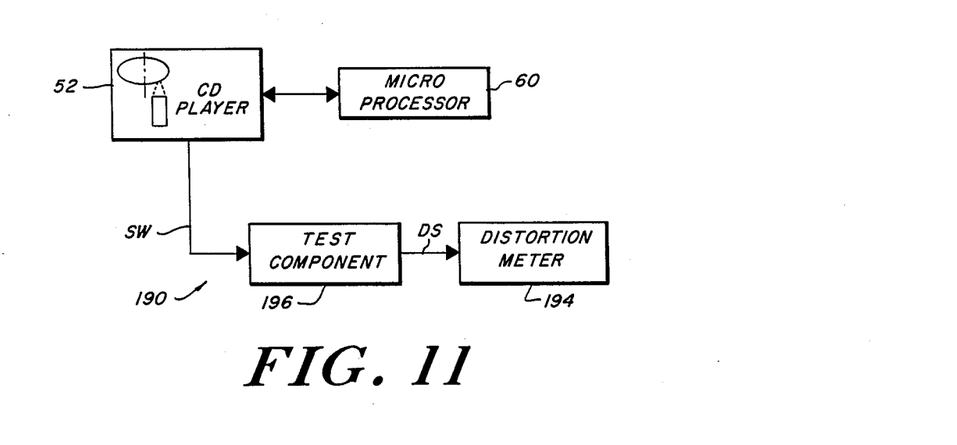
FIG. 11 is a schematic diagram of a system as shown in FIG. 9 in use for distortion factor measurements.

FIG. 11 shows a distortion measurement arrangement 190 for measuring the harmonic distortion of a pure sine wave signal in a component to be tested.

A signal generation system of the kind shown in FIG. 9 is again represented by a compact disc player 52 with an associated microprocessor 60. The output signal reproduced by the compact disc player 52 which is a pure sine wave signal SW is applied to the input of the test component 196. The output of the test component 192 is connected to a distortion meter 194 for measuring the distortion of the distorted signal DS resulting after passage of the pure sine wave signal through the test component 192.

Figure 12:
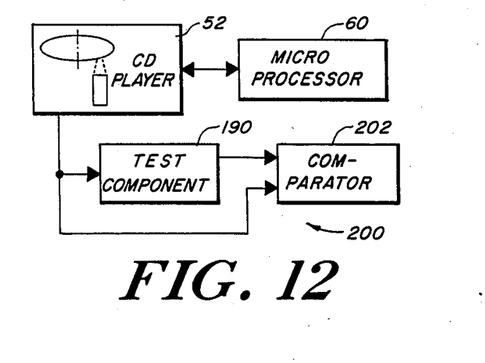
FIG. 12 is a schematic diagram of a system as shown in FIG. 9 in use for taking frequency response measurements.

FIG. 12 relates to the use of a signal generation system according to FIG. 9 for taking frequency response measurements. The signal generation system is again represented by compact disc player 52 and microprocessor 60. The compact disc player 52 is used to reproduce a stepped or continuous sequence of frequency signals of pure sine wave form throughout the frequency range to be considered with a predetermined intensity level. The output signal of the compact disc player 52 is applied both to the test component 190 to be measured and to a comparator 202. The output signal of the test component resulting after passage of the input frequency signal through said test component is also applied to the comparator. Thus, the signal attenuation factor of the test component may be measured for each frequency value so as to achieve the frequency response characteristic of the test component.

Figure 13:
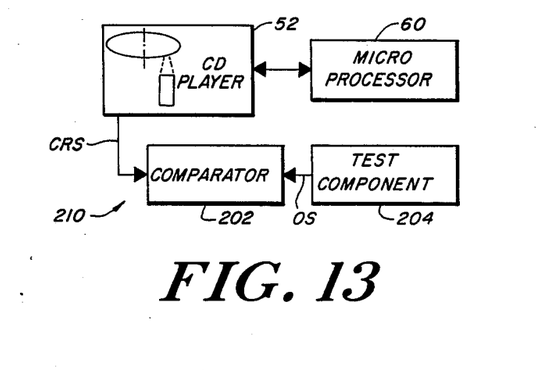
FIG. 13 is a schematic diagram of a system as shown in FIG. 9 in use for calibration purposes.

FIG. 13 shows a calibration arrangement 210 using a signal generation system of the kind shown in FIG. 9 again represented by compact disc player 52 and microprocessor 54. A calibration reference signal CRS is reproduced by the compact disc player 52 and applied to a first input of a comparator 202. A corresponding output signal OS of a test component 204 to be calibrated is applied to a second input of said comparator 202. Thus, the reference signal reproduced by the compact disc player 52 and the actual output signal of the test component are compared with each other and the test component may be adjusted and calibrated accordingly.

Figure 14:
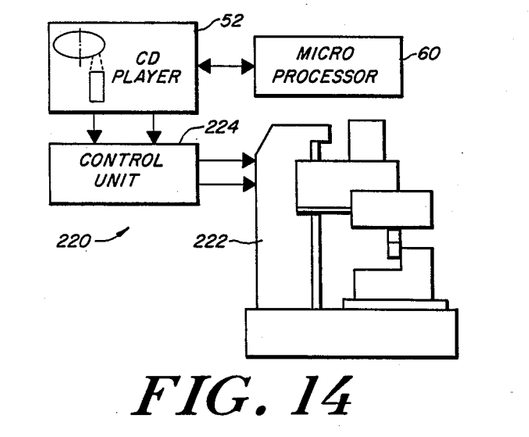
FIG. 14 is a schematic diagram of a system as shown in FIG. 9 in use for control of a numerical control machine tool.

Referring now to FIG. 14, there is shown an arrangement 220 using a signal generation system as shown in FIG. 9 in use for control of a numerical control machine tool 222. The signal generation system which is again represented by compact disc player 52 and microprocessor 60 generates digital or analog control signals and applies these signals to a control unit which controls the feed movements of the machine tool 222 schematically indicated in FIG. 14. The system may operate in a dual or multiple channel mode, as indicated by double lines, for independent control of several different feed mechanisms of the machine tool, for instance of longitudinal and transverse feed mechanisms and of a down feed mechanism.

Figure 15:
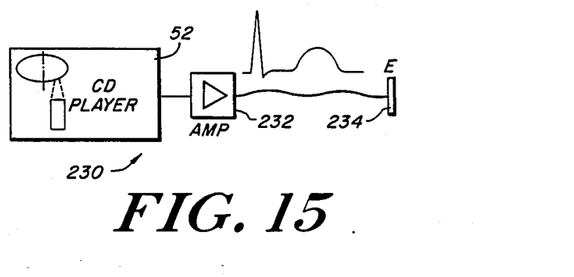
FIG. 15 is a schematic diagram of a sytem as shown in FIG. 9 in use for generation of high accuracy heart stimulation signals.

FIG. 15 shows the application of a signal generation system having a compact disc player 52 as a signal reproduction means in the medical field, namely for generation of heart stimulation signals. In contrast to prior art apparatus for heart stimulation, the compact disc player allows for reproduction of any desired wave form whatever in a very accurate manner, and thus, for generation of optimum stimulation signals. The output signal of the compact disc player 52 is amplified in an amplifier 232 and applied to an electrode 234. The stimulation signal may be closely adapted to the natural heart stimulation current wave form, as indicated in FIG. 15.

Figure 16:
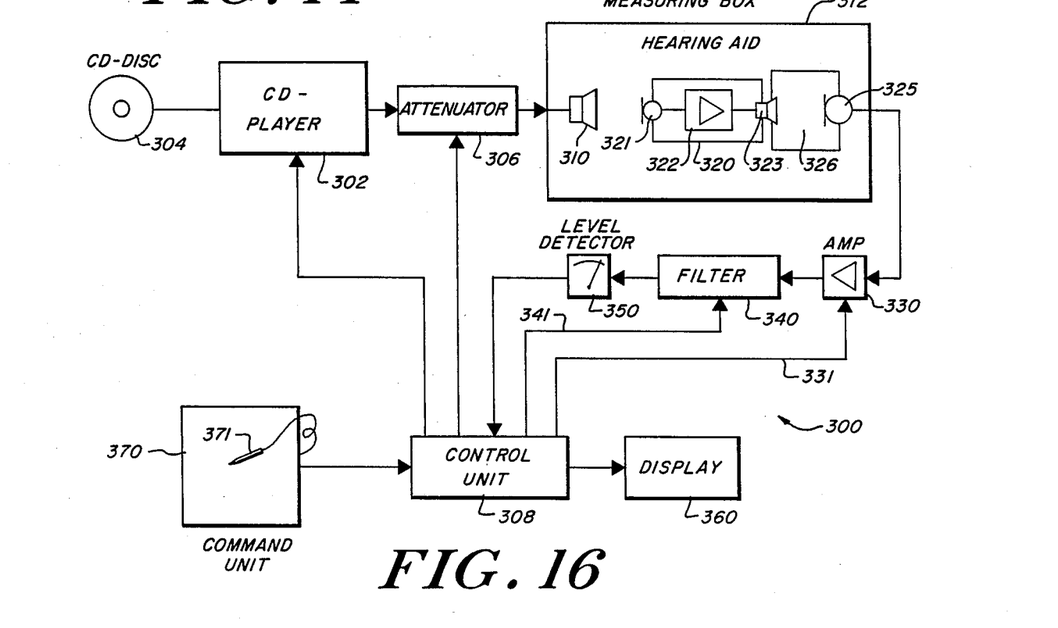
FIG. 16 is a block diagram of a system for measuring and adjusting hearing aids.

Finally, FIG. 16 shows a block diagram of an arrangement 300 for testing and adjusting hearing aids. The arrangement 300 includes a signal generation system according to the invention including a compact disc player 302 for reproducing test signals recorded in a digital form on a compact disc 304, an attenuator 306 for intensity control of the output signal of compact disc player 302 and a control unit 308 for controlling the operation of the arrangement. The output signal of the signal generation system, that is the output signal of attenutor 306, is applied to a loudspeaker 310 in a hearing aid measuring box 312. A hearing aid 320 to be tested is put into the measuring box 312 so that the input microphone 321 of the hearing aid will receive audible signals reproduced by loudspeaker 310. The input signal is processed by the hearing air circuit generally indicated by block 322 to produce an amplified output signal to the hearing aid's output loudspeaker 323. A microphone 325 is coupled to the output loudspeaker 323 of the hearing aid through a pneumatic coupling chamber 326 as is well known in the art to receive the acoustic output signals of the hearing aid. The output signals of the hearing aid received by microphone 325 are applied through an amplifier 330 and a filter 340 to a level detector 350. The amplifier 330, filter 340 and level detector 350 may be chosen from those well known in the art of hearing aid testing and may be controlled by control unit 308 as indicated by lines 331 and 341. Level detector 350 is connected to control unit 308 which has associated therewith a display unit 360 for display of the test results. Furthermore, control unit 308 has associated therewith a command unit 370 with a command probe 371 for manual selection of any of the test signals prestored on compact disc 304. the command unit 370 may be a tablet as described hereinbefore with reference to FIG. 5 or it may be a display screen unit as described hereinbefore with reference to FIG. 8 or any other suitable kind of command unit.

Hearing aid testing involves measurement of the output level, amplification, linear and nonlinear distortion of the signal and automatic gain control parameters such as attack time and release time. These measurements may be taken not only for the pupose of testing hearing aids but also to control proper adjustment of the hearing aid control means such as amplification control, frequency response control, automatic gain control adjustment means including means for adjusting the set point (input or output set point or both), slope of compression and time constants (attack or release time), and output limiter control for peak clipping of excessive amplitude signals. To perform the required testing measurements, several different kinds of test signals are used such as test frequency signals (from 63 Hz to 12.5 kHz), amplitude signals, various signal wave forms including pure tone signals, narrow and broad band noise or sweep frequency signals, or various signal modes such as a continuous on-signal mode or an on-off mode. Test signals of these various kinds are prestored as digital signal representations on compact disc 304 and may be reproduced by compact disc player 302 upon selection by command unit 370. The selection may be done in the same manner as with the audiometer system described hereinbefore.

What is claimed is:

1. An audiometer system adapted to selectively generate audiologic test signals of selectable kind and intensity, the system comprising:
   a digitally coded disc having a plurality of prestored audiologic test signals including those from the group of signals comprising pure tone signals, speech signals and noise signals of various frequencies and intensities prestored thereon as digital signal representations, each test signal having a corresponding unique address;
   a digital disc player including laser optical read out means for reproducing said prestored signals according to an address signal;
   control means having a memory for storing at least one control program and a table listing the addresses of said prestored test signals;
   selection means for manually selecting said prestored test signals including a tablet on which a schedule of identifications of the available prestored test signals is provided, said tablet having associated therewith a command probe movable on said tablet for manual selection of ones of said identifications of said test signals; and
   said control means receiving identification data from said command probe and being operative to address said means for reproducing said prestored signals.

2. The system according to claim 1, wherein said digital disc player comprises one of a compact disc audio player and a video disc player.

3. The system according to claim 1, wherein said means for reproducing comprises a dual channel means for reproducing, wherein one channel is adapted to selectively generate audiologic test signals and the other channel is adapted to selectively generate audiologic mask signals.

4. The system according to claim 1, comprising a device for protecting the examinee against excessive intensity signals, said device having means for monitoring the examinee and means for decreasing the intensity of the signals reproduced by said means for reproducing when an excessive intensity of said test signal is indicated by said examinee.

5. The system according to claim 4, wherein said means for monitoring comprises an electro-acoustic transducer activating said means for decreasing the intensity when a cry of the examinee is received.

6. The system according to claim 1, wherein said indications on said tablet are provided both in a visual form and in a computer readable form, said command probe being adapted to read said identifications and to provide a respective address signal to said means for reproducing.

7. The system according to claim 1, wherein said command probe is adapted to activate the tablet by touching said tablet at a selected identification, causing said tablet to provide a respective address signal to said means for reproducing.

8. The system according to claim 1, wherein said tablet comprises x-y-grid means adapted to be operable in response to said probe using one of mechanicaal pressure, magnetic, inductive, or capacitive coupling.

9. The system according to claim 1, wherein said tablet includes a frame for holding a printed form sheet, said sheet comprising one of paper, plastic and foil material, said form sheet having printed data thereon representative of said schedule of identifications, said form sheet further serving as a record sheet for a record of test results.

10. The system according to claim 9, wherein at least two different kinds of printed form sheets are provided, said different kinds of form sheets having different printed data thereon and being provided with a binary code index, and wherein said frame includes form recognition means adapted to recognize the presence and the kind of a form sheet on said tablet.

11. The system according to claim 10, wherein said form recognition means comprises optical sensing means.

12. The system according to claim 11 wherein said binary code index is printed on the form sheet and said optical sensing means comprise miniature reflection photoelectric devices including a light-emitting diode and an adjacent lightsensitive semiconductor element responsive to reflected light.

13. The system according to claim 11, wherein said binary code index is punched into the form sheet and said optical sensing means comprise light-emitting elements arranged at one side of the form sheet to direct a light beam thereon and light-sensitive elements arranged at the opposite side of the form sheet to receive light transmitted through index punchings in the form sheet.

14. The system according to claim 11, further comprising an interval timer circuit operating said optical sensing means only during successive short periods with intervals therebetween.

15. The system according to claim 10, wherein said printed form sheet includes grooves for guiding said probe during manual movement thereon.

16. The system according to claim 1, wherein said tablet further includes grooves for guiding said probe during manual movement thereon.

17. The system according to claim 1, wherein said tablet further comprises a transparent cover sheet including one of slots and punched grooves for guiding said command probe.

18. An audiometer system adapted to selectively generate audiologic test signals of selectable kind and intensity, the system comprising:
a digitally coded disc having a plurality of prestored audiologic test signals including those from the group of signals comprising pure tone signals, speech signals and noise signals of various frequencies and intensities prestored thereon as digital signal representations, each test signal having a corresponding unique address;
a digital disc player having means including laser optical read out means for reproducing said prestored signals in response to an address signal;
control means having a memory for storing at least one control program and a table listing the addresses of said test signals; and
selection means including a display screen adapted to display a schedule of visual identification of available test signals on said screen, said screen having associated therewith identification means adapted to selectively identify one of said identifications displayed thereon so as to provide a respective identification signal; wherein
said control means receiving said identification signal from said display screen unit and being operative to address said means for reproducing said prestored signals.

19. The system according to claim 18, wherein said identification means comprises a cursor movable on said screen, and a control device for controlling movement of said cursor on said display screen.

20. The system according to claim 19, wherein said control device comprises a keyboard.

21. The system according to claim 19, wherein said control means includes a control lever adapted to be moved in an x-y-system causing a corresponding movement of said cursor.

22. The system according to claim 19, wherein said control means comprises a sensor unit operable in combination with an identification raster plate wherein said sensor unit is freely movable on said raster plate and generates in response to its movement on said raster plate a control signal causing said cursor to be moved accordingly.

23. The system according to claim 18, wherein said identification means comprises a probe having means to provide an address signal by touching said screen at the region displaying the identification to be selected.

* * * * *